United States Patent
Snedden et al.

(10) Patent No.: US 8,695,611 B2
(45) Date of Patent: Apr. 15, 2014

(54) DUAL TIP ORAL CARE IMPLEMENT

(75) Inventors: John Snedden, Sandpoint, ID (US); Les Greer, Jr., Sandpoint, ID (US)

(73) Assignee: Unicep Packaging, Inc., Sandpoint, ID (US)

( * ) Notice: Subject to any disclaimer, the term of this patent is extended or adjusted under 35 U.S.C. 154(b) by 274 days.

(21) Appl. No.: 12/829,254

(22) Filed: Jul. 1, 2010

(65) Prior Publication Data

US 2012/0000483 A1    Jan. 5, 2012

(51) Int. Cl.
*A45D 44/18*    (2006.01)

(52) U.S. Cl.
USPC .......................................................... 132/309

(58) Field of Classification Search
USPC .......................................... 132/309, 321, 329
See application file for complete search history.

(56) References Cited

U.S. PATENT DOCUMENTS

| | | | | |
|---|---|---|---|---|
| 4,922,936 | A * | 5/1990 | Buzzi et al. | 132/321 |
| 5,184,719 | A * | 2/1993 | Gordon | 206/209.1 |
| 5,701,921 | A * | 12/1997 | Father et al. | 132/309 |
| 6,015,293 | A * | 1/2000 | Rimkus | 433/141 |
| D527,528 | S | 9/2006 | Hohlbein | |
| D528,803 | S | 9/2006 | Hohlbein | |
| D532,202 | S | 11/2006 | Hohlbein | |
| D532,607 | S | 11/2006 | Hohlbein | |
| 7,182,542 | B2 | 2/2007 | Hohlbein | |
| D557,504 | S | 12/2007 | Hohlbein | |
| D557,505 | S | 12/2007 | Hohlbein | |
| 7,331,731 | B2 | 2/2008 | Hohlbein et al. | |
| 7,478,959 | B2 | 1/2009 | Hohlbein | |
| 7,722,274 | B2 | 5/2010 | Hohlbein et al. | |
| 2005/0118553 | A1 | 6/2005 | Lagos Galvan | |
| 2006/0048790 | A1 * | 3/2006 | Petner | 132/309 |
| 2006/0260080 | A1 | 11/2006 | Hsu | |
| 2008/0120798 | A1 | 5/2008 | Sorrentino et al. | |
| 2009/0178219 | A1 | 7/2009 | Hohlbein | |
| 2009/0320224 | A1 | 12/2009 | Hohlbein et al. | |
| 2009/0320226 | A1 | 12/2009 | Robinson et al. | |

FOREIGN PATENT DOCUMENTS

| | | |
|---|---|---|
| WO | WO2004021914 A2 | 3/2004 |
| WO | WO2005110149 A2 | 11/2005 |
| WO | WO2007076405 A1 | 7/2007 |

* cited by examiner

*Primary Examiner* — Rachel Steitz
(74) *Attorney, Agent, or Firm* — Lee & Hayes, PLLC

(57) ABSTRACT

A disposable oral care implement that provides various oral care functions in a compact form is disclosed therein. The disposable oral care implement includes a body, a polishing block attached to a first end of the body, and one or more oral care tools coupled to a second end of the body. The one or more oral care tools may include a tongue scrapper, an interdental pick, a brush, a floss holder, and/or a gum stimulator. The body of the disposable oral care implement may be formed by injection molding. The oral care tool may be formed on the second end of the body by over-molding while the polishing block may be attached to the first end of the body by way of press-fit.

22 Claims, 7 Drawing Sheets

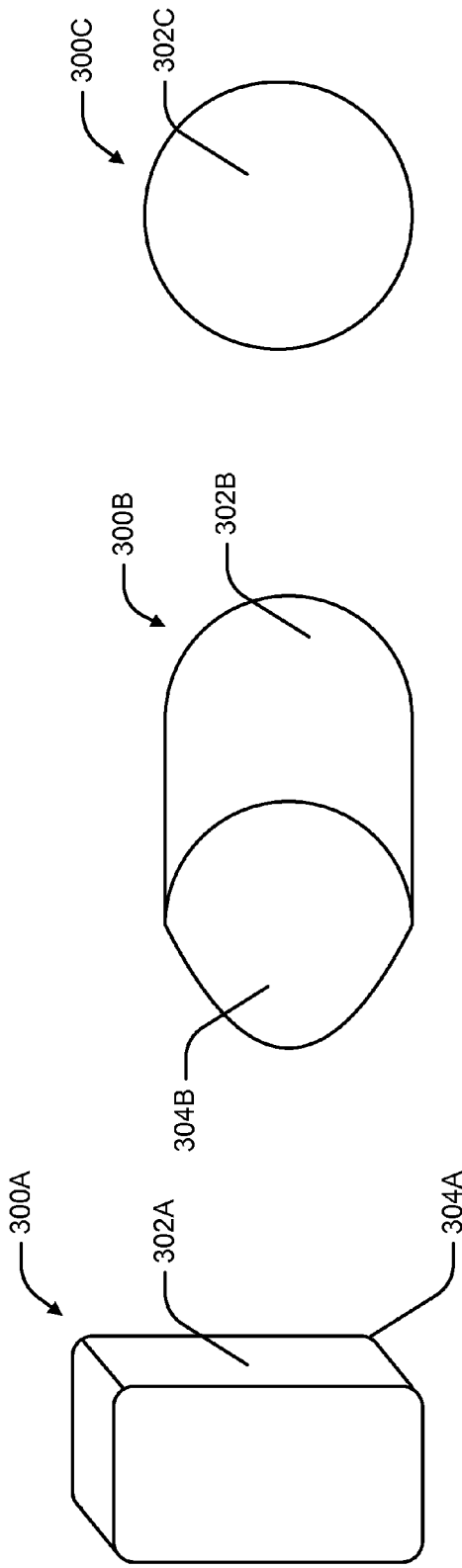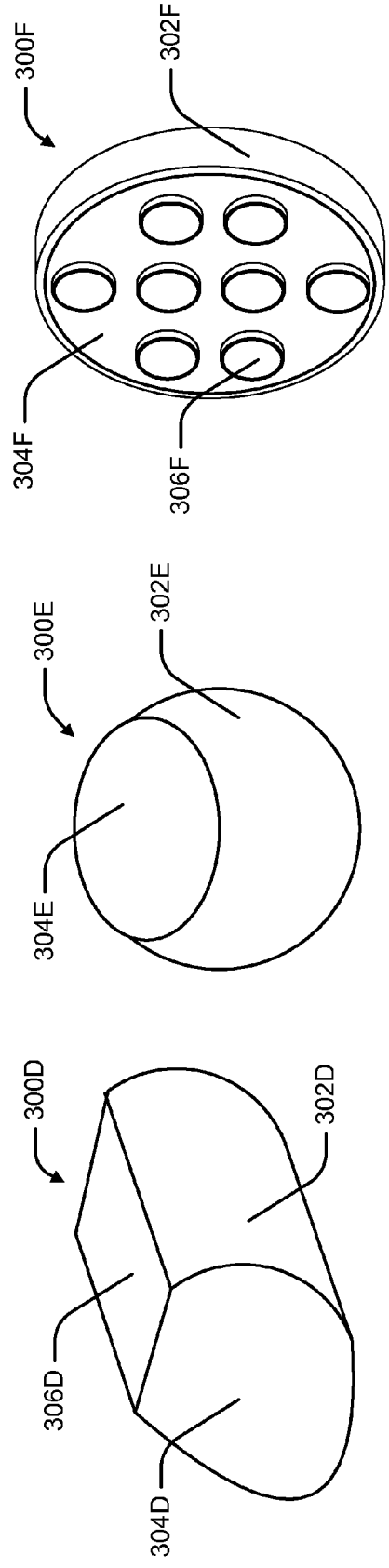

DUAL TIP ORAL CARE IMPLEMENT

BACKGROUND

Disposable oral care products have long become a part of daily lives of people. Today, many people use disposable oral care products such as disposable toothpicks on a daily basis. These people may choose to use a disposable oral care product for hygienic reasons. As the cost of a disposable oral care product is normally lower compared with that of a regular oral care product, people can simply dispose of the disposable oral care product after use and employ a new disposable oral care product each day, for example. Furthermore, the disposable oral care products can provide convenience to daily lives of the people, especially for people who need to travel but do not want to carry along with their oral care products during their trips. Due to their relatively low-cost and popular nature, people can easily purchase a disposable oral care product at any convenience or grocery store. Moreover, travel accommodations such as hotels often provide disposable oral care products for their tenants in each room. This further contributes to the popularity of disposable oral care products in the market.

Given their popularity, developments have been made to improve disposable oral care products. However, these disposable oral care products are still limited in their ability to clean teeth. Although some recent oral care products may provide oral care functions other than cleaning teeth, they are less accessible to the general public. Furthermore, the oral care functions of these products are limited to certain combinations of oral care functions.

SUMMARY

This Summary is provided to introduce simplified concepts of disposable oral care implements that can provide multiple functions in a single compact form. The disposable oral care implements are further described below in the Detailed Description. This Summary is not intended to identify key features or essential features of the claimed subject matter, nor is it intended to be used as an aid in determining the scope of the claimed subject matter.

In one embodiment, the disposable oral care implement comprises a body, a rounded foam block that is connected to a first end of the body, and an inter-dental pick that is coupled to a second end of the body. The inter-dental pick may have a central body which includes a plurality of conically shaped spikes that project radially outward from the central body. In one embodiment, the rounded foam block usable with the disposable oral care implement may further include an oral care material disposed on and/or around the rounded foam block, and may be configured to polish a surface.

In another embodiment, the disposable oral care implement comprises a body, a polishing block that is attached to a first end of the body, and an inter-dental pick that is coupled to a second end of the body. The polishing block may include an oral care material and may be configured to polish a surface. In one embodiment, the oral care material may include an oral cleaning strip. The inter-dental pick may include a floss holder to hold a dental floss. Alternatively, the inter-dental pick may include a central body which has bristles projecting outward from the central body.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference number in different figures indicates similar or identical items.

FIG. 3A, FIG. 3B, FIG. 3C, FIG. 3D, FIG. 3E and FIG. 3F illustrate perspective views of other example polishing blocks usable with a disposable oral care implement according to the present disclosure.

DETAILED DESCRIPTION

Overview

Figure 1A:
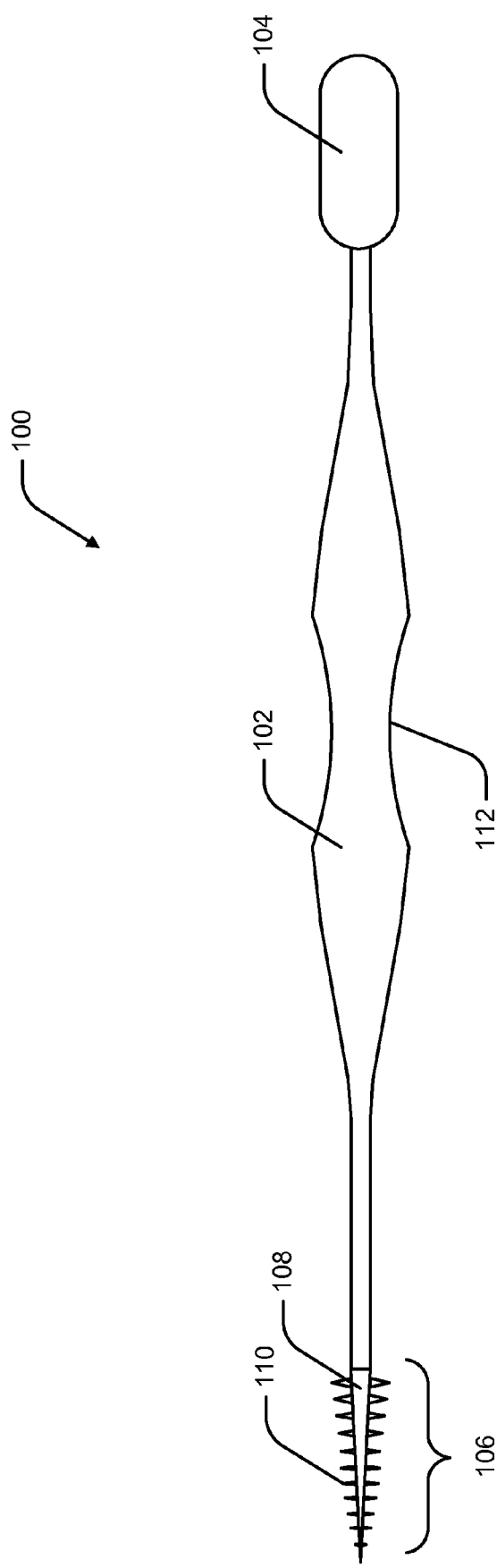
FIG. 1A and FIG. 1B illustrate a side view and a top view respectively of an example disposable oral care implement in accordance with the present disclosure.

As discussed above, disposable oral care implements are often limited in their ability to clean, polish, and remove residue from teeth. Even though oral care products having other oral care functions may exist, they are still limited to certain functional combinations. This disclosure describes disposable oral care implements that provide multiple functions in a single compact form.

The oral care implements described herein are primarily in the context of oral care implements for disposable use. However, the disclosed oral care implements may be used as oral care implements that are intended to be used for a long period of time, say, a week, a month or a year, for example. Moreover, while the oral care implements described herein are described as being applicable in the oral care industry, numerous other industries may also benefit from the disclosed oral care implements. By way of example and not limitation, the oral care implements described herein may be used in the fields of cleaning such products as glassware, laboratory apparatuses, machinery parts, and the like.

In general, the oral care implements as described in this disclosure include a body, a polishing block connected to a first end of the body, and one or more oral care tools coupled to a second end of the body. The one or more oral care tools may comprise a tool providing a different or same oral care function of the polishing block. By way of example and not limitation, the oral care tool may comprise a tongue scrapper, an inter-dental pick, a brush, a floss holder and/or a gum stimulator. While the polishing block and the oral care tools are described as being fixed to the body, in some embodiments the polishing block and/or oral care tools may be selectively removable so as to be interchangeable to reconfigure the oral care implement. In one example, an oral care implement may be packaged with a plurality of interchangeable polishing blocks and/or oral care implements that can be coupled to the body in any combination desired by a user.

The embodiments described herein employ a foam material, a spongy-like material, a porous material or the like, for the polishing block, and a plastic material for the body and the one or more oral care tools. However, in other embodiments, other materials may be used. Moreover, one or more coatings, surface treatments, or finishes may be applied. For example, microstructures and/or nanostructures may be applied to the polishing block, the body and/or the oral care tool to improve their efficacy.

In addition to providing multiple oral care functions in a compact form, the oral care implements described herein may also provide convenience to users by allowing the implements to be foldable for saving storage space and/or extendable for accommodating different palm sizes of the users.

These and other aspects of the oral care implements will be described in further detail below with reference to several illustrative embodiments.

Illustrative Oral Care Implement

Figure 1B:
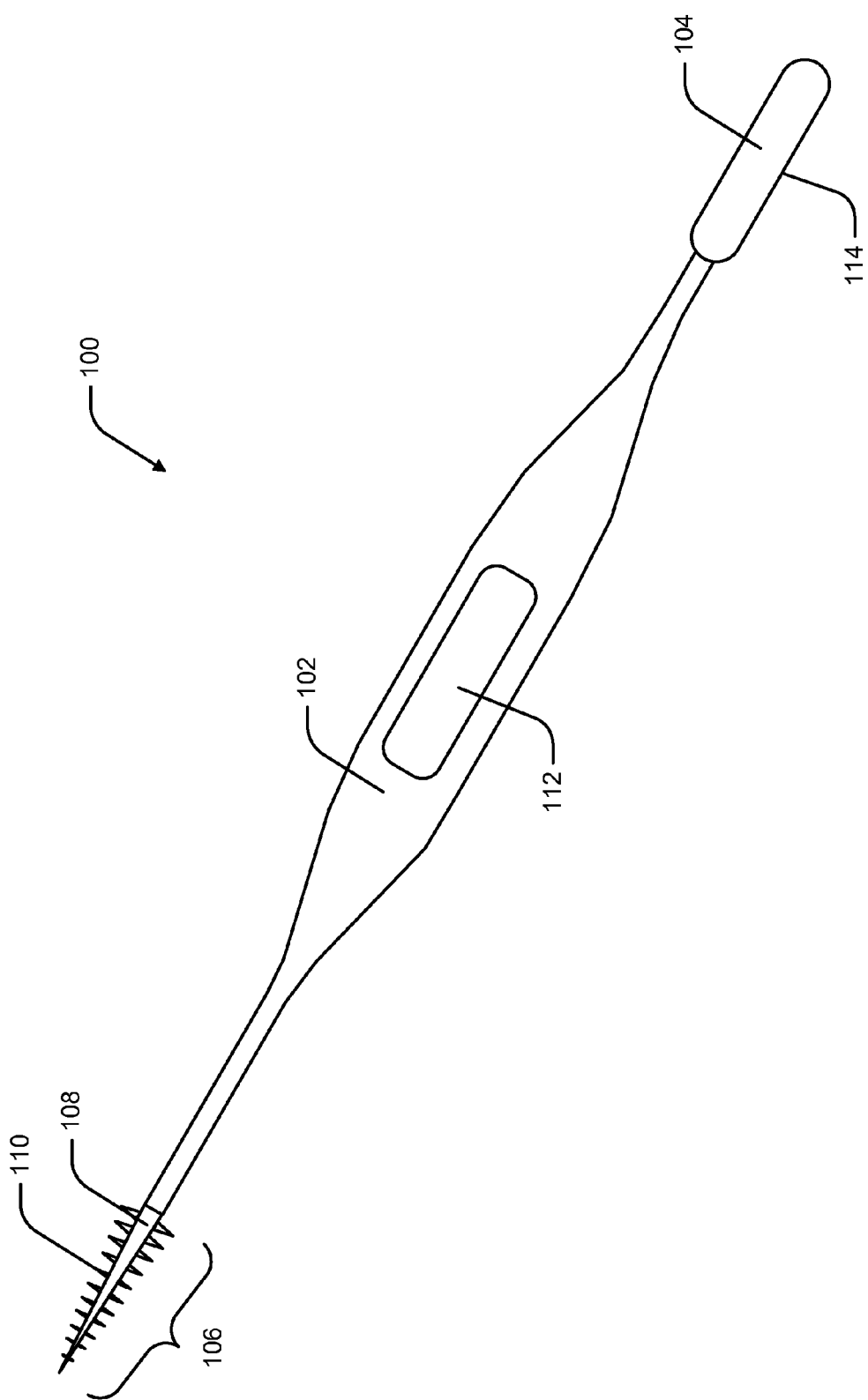

FIG. 1A and FIG. 1B are a side view and a top view respectively of an example disposable oral care implement 100. The oral care implement 100 comprises a body 102, a rounded foam block 104, and an inter-dental pick 106. The rounded foam block 104 is connected to a first end of the body 102 and the inter-dental pick 106 is coupled to a second end of the body 102. The inter-dental pick 106 includes a central body 108 having a plurality of soft, elastomeric spikes 110 projecting radially outward from the central body 108. The central body 108 can be of different shapes and sizes. In one embodiment, the central body 108 includes a cylindrical shape. In other embodiments, the central body 108 may include a conical shape, a triangular wedge shape, a thin sheet or strip-like shape. The plurality of spikes 110 of the central body 108 may include, but are not limited to, conically shaped spikes, cylindrically shaped spikes, or both. The plurality of spikes 110 may project radially outward from the central body 108 in one or more directions. In one embodiment, all of the plurality of spikes 110 project radially outward from the central body 108 in a specific direction. In another embodiment, at least some of the plurality of spikes 110 project radially outward from the central body 108 in one direction while the rest of the plurality of spikes 110 are projecting in the opposite direction. In some embodiments, the plurality of spikes 110 project in three specific directions with about one-third of the plurality of spikes 110 projecting in each of the three directions. In still another embodiment, the plurality of spikes 110 can project radially outward from the central body 108 in four different directions with about one-fourth of the plurality of spikes 110 in each direction. The inter-dental pick 106 may be configured to clean a cavity between surfaces. For example, the inter-dental pick 106 may be used to clean between teeth after a meal.

The inter-dental pick 106 may include a first oral care material disposed thereon. The first oral care material may include a gel material, a paste material, or a strip material. The first oral care material may be applied to surfaces or a cavity between the surfaces when the inter-dental pick 106 is applied to clean between the surfaces.

The body 102 of the oral care implement 100 may optionally include an indentation 112 to facilitate gripping of the body 102. In one embodiment, the indentation 112 may be located at the center of the body 102. Alternatively, the indentation 112 may be located at a position closer to the first end of the body 102 or the second end of the body 102. Moreover, the body 102 may have more than one indentation 112. The indentation 112 may be made of the same or different material as the body 102. In one embodiment, the indentation 112 may be made from a softer material for comfortable gripping.

The rounded foam block 104, as shown in FIG. 1A and FIG. 1B, is configured to polish a surface. The surface to be polished by the rounded foam block 104 may include, for example, a tooth surface, a tongue surface, a mouth cavity surface, a gum surface, or any combination thereof. In one embodiment, the rounded foam block 104 may include a second oral care material disposed on and/or around the rounded foam block 104. The second oral care material may include an oral cleaning strip, a gel material, or a paste material. For example, the first oral care material may be applied to a tooth surface when brushing the tooth surface with the rounded foam block 104. In an alternative embodiment, the second oral care material may be a separate entity, completely separated or detached from the rounded foam block 104 or the oral care implement 100. A user may first apply the second oral care material, e.g., an oral cleaning strip, to a tooth surface, and use the rounded foam block 104 to clean the tooth surface. The second oral care material on the rounded foam block 104 may be of a different or same material as the first oral care material on the inter-dental pick 106.

The rounded foam block 104 may additionally or alternatively include a powder material. The powder material may comprise an abrasive material, a breath freshening material, or both. Additionally or alternatively, the rounded foam block 104 may be impregnated with a liquid material, a gel material or a paste material. For example, the rounded foam block 104 may be used to polish/wash a mouth cavity surface using the powder material and/or the liquid material. Thus, the oral care implement 100 may be effectively used to clean between teeth and stimulate gums using the inter-dental pick 106, and to polish teeth and freshen breath using the foam block 104.

The rounded foam block 104 may include a flat surface 114. The flat surface 114 is configured to facilitate holding of a powder material, a gel material or a paste material applied on the rounded foam block 104.

Figure 2A:
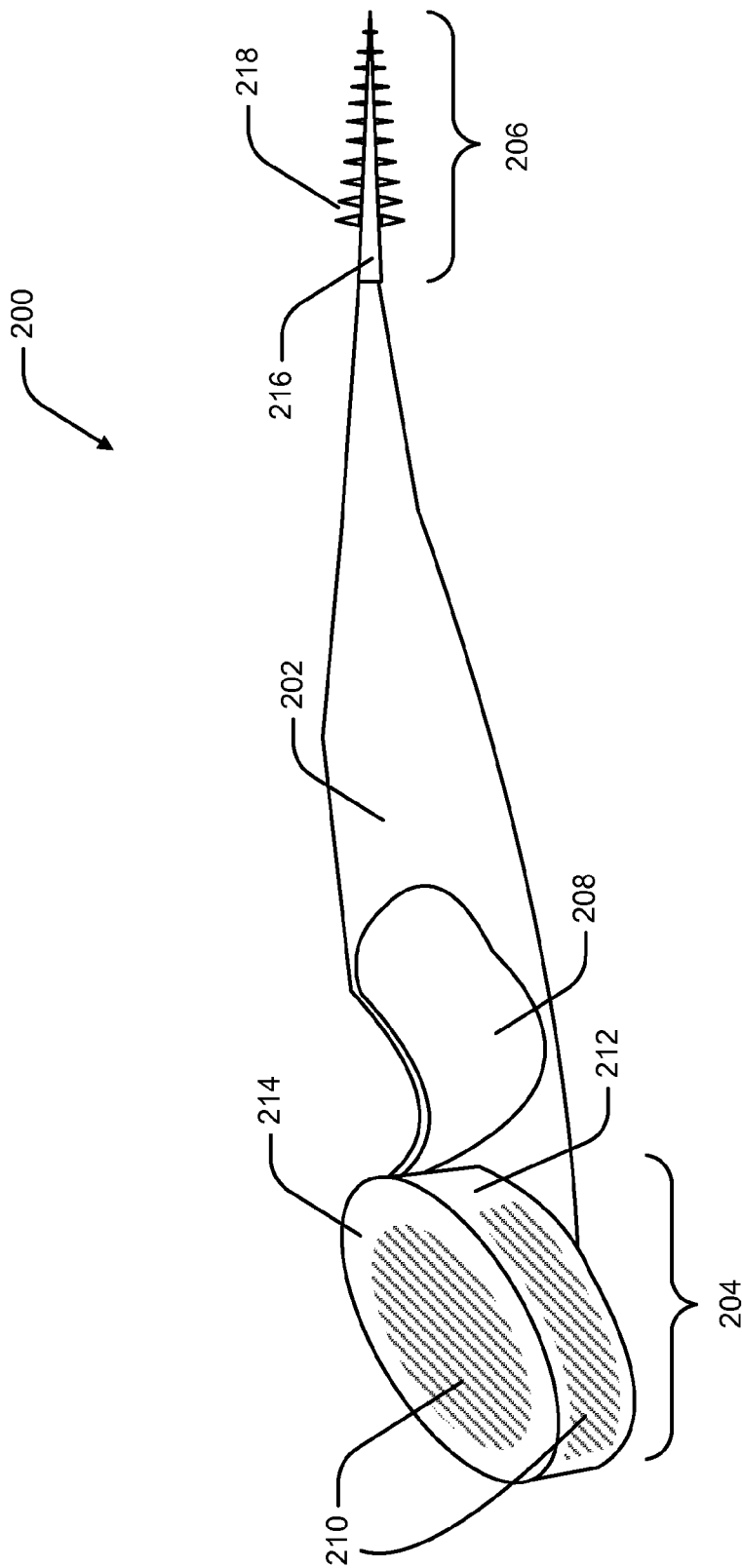
FIGS. 2A and 2B illustrate a perspective view and a side view respectively of another example disposable oral care implement in accordance with the present disclosure.
Figure 2B:
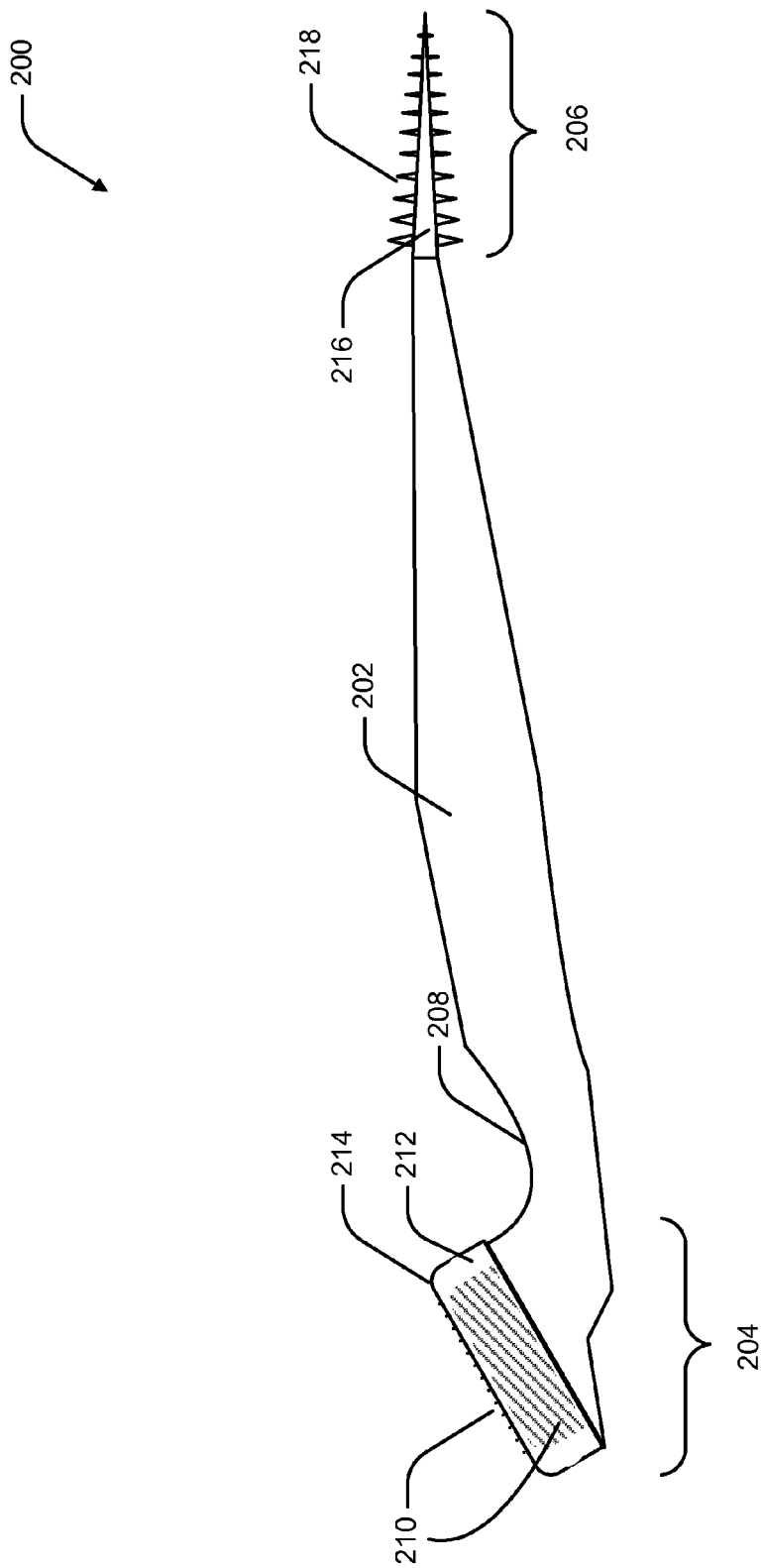

FIGS. 2A and 2B are a perspective view and a side view respectively of another example disposable oral care implement 200. The oral care implement 200 comprises a body 202, a polishing block 204 attached to a first end of the body 202, and an inter-dental pick 206 coupled to a second end of the body 202. The body 202 may optionally include an indentation 208. The polishing block 204 may include an oral care material 210 disposed on and/or around the polishing block 204, and is configured to polish a surface which includes, for example, a tooth surface, a tongue surface, a mouth cavity surface, a gum surface, or any combination thereof. The oral care material 210 may comprise an oral cleaning strip, a gel material, a paste material, or a powder material, for example. Alternatively, the oral care material 210 may be a separate entity, and completely separated or detached from the polishing block 204 or the oral care implement 200. In some embodiments, the polishing block 204 may additionally or alternatively be configured to be impregnated with a liquid material, a gel material, a paste material, or any combination thereof. In FIG. 2A and FIG. 2B, the polishing block 204 may include an elliptical body 212 having a flat surface 214 to hold the oral care material 210 as shown in FIGS. 2A and 2B.

Although FIG. 2A and FIG. 2B show that the polishing block 204 includes an elliptical body 212 having a flat surface 214, the polishing block 204 may take on any other shape and/or size. FIG. 3A, FIG. 3B, FIG. 3C, FIG. 3D, FIG. 3E and FIG. 3F are perspective views of other example polishing blocks of the disposable oral care implement. For example, FIG. 3A shows a polishing block 300A including a generally rectangular body 302A having rounded edges 304A to facilitate holding of a powder material, for example. FIG. 3B shows a polishing block 300B including a cylindrical body 302B having a spherical cap 304B on a surface of the cylindrical body 302B. The polishing block 300B can facilitate a smooth contact with a surface to be polished through its curved surface. FIG. 3C shows another example polishing block 300C including a spherical body 302C that can provide a smoother contact with a surface such as a mouth cavity surface.

The example polishing blocks 300B and 300C may further be modified in some embodiments. For example, FIG. 3D shows a polishing block 300D including a cylindrical body 302D having a spherical cap 304D. The polishing block 300D further includes a flat surface 306D to facilitate holding of a powder material, a gel material, a paste material, or any combination thereof. FIG. 3E shows a polishing block 300E including a spherical body 302E having a flat surface 304E. The polishing blocks 300D and 300E allow polishing/washing a first type of surface using the flat surface portion (i.e., 306D and 304E) and polishing/washing a second type of surface using the other part of the polishing block (i.e., curved surface portion of the body). For example, the polishing block may be configured to polish the teeth using the flat surface portion and wash/polish the mouth cavity surface using the curved surface portion.

FIG. 3F shows a polishing block 300F including an elliptical body 302F having a flat surface 304F. The polishing block 300F as illustrated further comprises a plurality of raised protrusions/projections 306F on the flat surface 304F. These raised protrusions/projections 306F may be made of the same or different material as that of the elliptical body 302F. In one embodiment, the protrusions/projections 306F are made of a softer or harder material than that for the flat surface 304F to allow different levels of deformation when the polishing block 300F is pressed against a surface to be polished. This allow the flat surface 304F or the oral care material (e.g., a powder material) on the flat surface 304F to have a better contact with the surface to be polished while the oral care material is reasonably held or trapped between the protrusions/projections 306F. Additionally or alternatively, the raised protrusions/projections 306F themselves may be made of different materials with the material used for the protrusions/projections 306F located in the surrounding being softer than the material used for the protrusions/projections 306F located at the center. This allows different levels of pressure and/or contact applied to surface(s) to be polished. For example, the oral care implement (or the polishing block 300F) may be used for washing/polishing a tooth surface. Using this configuration of the polishing block 300F, a gum surface, which is more delicate than the tooth surface to be polished, can be cleaned with the softer surrounding protrusions/projections 306F at the same time while the tooth surface is polished/washed using the harder protrusions/projections 306F at the center. Using a softer material for a gum surface while using a harder material for a tooth surface, for example, helps to treat surfaces of different levels of delicacy differently (e.g., by applying different pressures on the surfaces of different levels of delicacy through using materials of different softness) at the same time. Although FIG. 3F shows that the raised protrusions/projections 306F are in the same height, the raised protrusions/projections 306F may be of different heights. In some embodiments, the heights of the protrusions/projections 306F are gradually reduced from the center to the surrounding or vice versa.

Returning back to FIG. 2A and FIG. 2B, the inter-dental pick 206 may include a central body 216 having a plurality of spikes 218 projecting radially outward from the central body 216. The central body 216 may be of different shapes and/or sizes. In one embodiment, the central body 216 may include a cylindrical shape. In another embodiment, the central body 216 may include a conical shape. In still other embodiments, the central body 216 may include a triangular wedge shape, a thin sheet or strip-like shape. The plurality of spikes 218 of the central body 216 may include, for example, conically shaped spikes, cylindrically shaped spikes, or both.

In alternative embodiments, the disposable oral care implement may include other types of inter-dental picks. For example, FIG. 4A shows an inter-dental pick 400A including a floss holder 402A to hold a dental floss 404A. Although being shown to be Y-shaped, the floss holder 402A may take on any other shape and/or size. For instance, the floss holder 402A may be U-shaped or F-shaped.

Figure 4B:
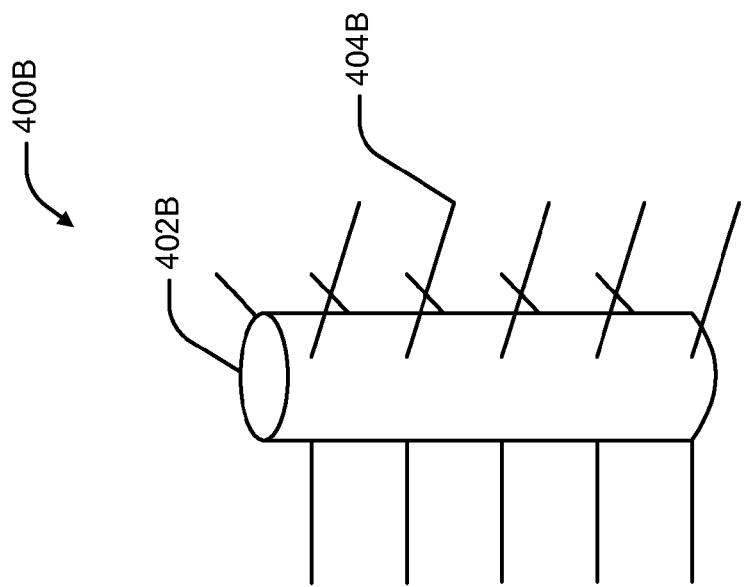
FIG. 4A and FIG. 4B illustrate perspective views of other example inter-dental picks usable with a disposable oral care implement according to the present disclosure.
Figure 4A:
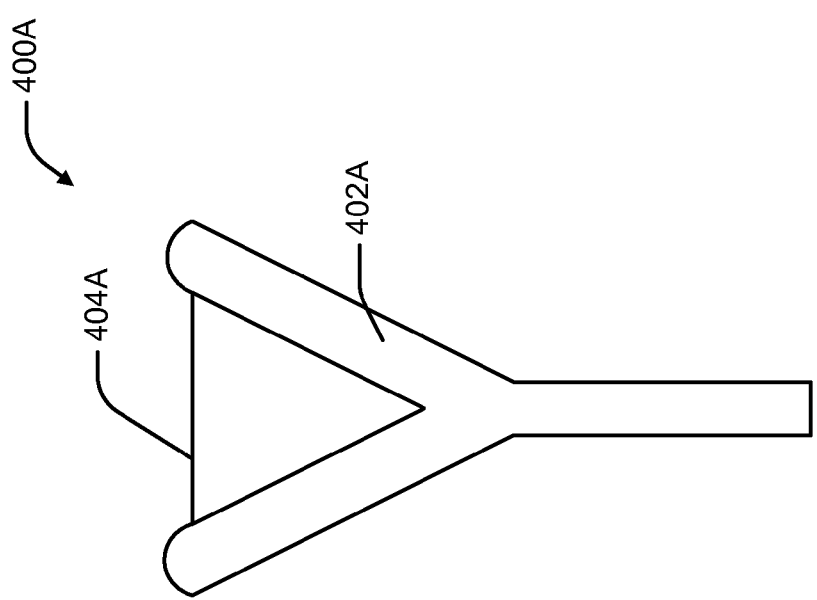

FIG. 4B shows another example inter-dental pick 400B usable with the disposable oral care implement. The inter-dental pick 400B includes a central body 402B having a plurality of bristles 404B projecting outward from the central body 402B. The central body 402B may take on any shape and/or size. The central body 402B may include, for example, a cylindrical shape, a conical shape, a triangular wedge shape, a thin sheet or strip-like shape, or any combination thereof. Furthermore, the plurality of bristles 404B may project radially outward from the central body 402B in one or more directions. In one embodiment, all of the plurality of bristles 404B project radially outward from the central body 402B in a specific direction. In another embodiment, at least some of the plurality of bristles 404B project radially outward from the central body 402B in one direction while the rest of the plurality of bristles 404B project in the opposite direction. In some embodiments, the plurality of bristles 404B project in three specific directions with about one-third of the plurality of bristles 404B projecting in each of the three directions. In still another embodiment, the plurality of bristles 404B may project in four different directions with about one-fourth of the plurality of bristles 404B projecting in each direction.

Alternative Embodiments of Disposable Oral Care Implements

Although the above example disposable oral care implements are described to include an inter-dental pick coupled to one end of a body, the disposable oral care implements are not limited thereto. For example, a disposable oral care implement may include a body having a polishing block attached to a first end of the body, and one or more other oral care tools coupled to a second end of the body. In this embodiment, the polishing block may include any of the features/configurations of the polishing blocks described in the above embodiments, such as sizes, shapes, materials, polishing and/or breath-functioning compositions, and the like.

The oral care tool may comprise a tongue scrapper, an inter-dental pick, a brush, a floss holder, and/or a gum stimulator. If the oral care tool is an inter-dental pick, the inter-dental pick may include any of the features/configurations described in the preceding embodiments.

Furthermore, the body of any example disposable oral care implement described above may not necessarily be of a single piece. In one embodiment, the body of the disposable oral care implement may be foldable to save a storage space required for storing the oral care implement. For example, the body may comprise two pieces with a joint therebetween. Additionally or alternatively, the body of the disposable oral care implement may be extendable to accommodate/adapt various palm sizes of different people. For example, an adult may want a disposable oral care implement with a longer body while a child may prefer a disposable oral care implement with a shorter body for easy handling. Therefore, instead of having one-size-fit-all body for all disposable oral care implements or various disposable oral care implements comprising different sizes of the body, the disposable oral care implement may be made extendable to accommodate various needs of the people. Additionally or alternatively, the body of any example disposable oral care implement may include a soft gripping surface for easy gripping of the disposable oral care implement.

Example Production Process of Disposable Oral Care Implements

Figure 5:
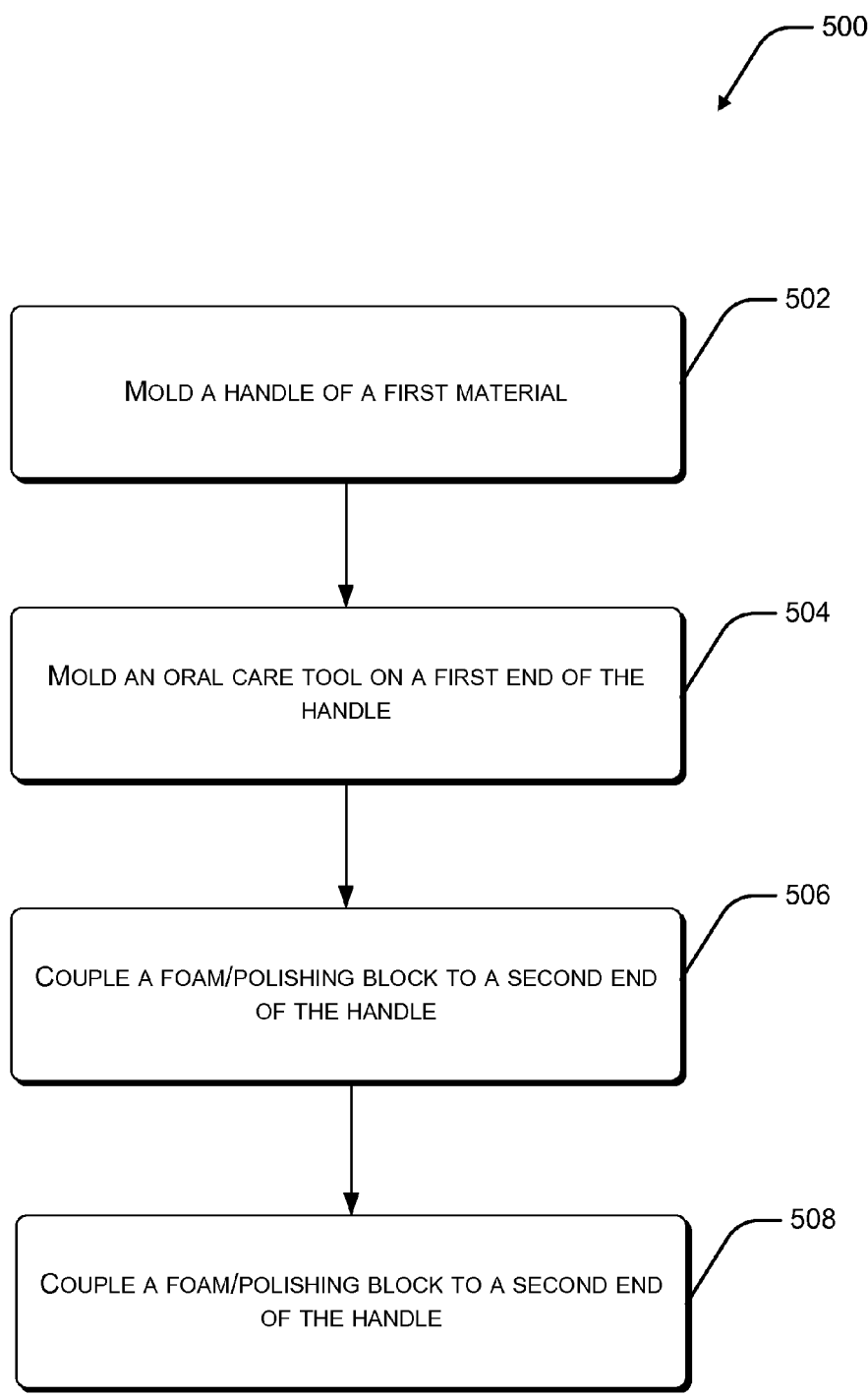
FIG. 5 illustrates an example process of producing a disposable oral care implement in accordance with the present disclosure.

FIG. 5 is an example process 500 of producing the disposable oral care implements. The process 500 may be performed to make a disposable oral care implement using a single material or a plurality of different materials. For example, the different parts of a disposable oral care implement may be formed of a polymer such as polyethylene, polypropylene, ethyl vinyl alcohol copolymer or any other suitable polymer, mixture or the like that is suitable for forming the disposable oral care implement. In some alternative embodiments, the various parts of the disposable oral care implement may be formed of one or more other materials, and may have one or more coatings or finishes (e.g., microstructures and/or nanostructures).

In this description, the order in which the process is described is not intended to be construed as a limitation, and any number of the described process blocks may be combined in any order to implement the process, or an alternate process. The process is described as follows.

Block 502 represents molding a body of a first material. The body may be molded in a first mold. The first mold comprises a shape to form a body of a disposable oral care implement. By way of example and not limitation, the first material can be disposed into the first mold by injection molding.

Block 504 represents molding an oral care tool or some portions of the oral care tool on a first end of the body. The oral care tool may be made of a second material. The second material may comprise the first material, a material softer than the first material, or a material harder than the first material. The second material may be molded onto the first end of the body by over-molding or co-molding. For example, Block 520 may mold a plurality of spikes on the first end of the body.

Block 506 represents coupling a foam/polishing block to a second end of the body. The coupling of the foam block to the second end of the body can be achieved by press fit, adhesion, snap fit, barbs, and/or sonic or heat welding. The foam blocks themselves may be machined/punched, stamped, or otherwise cut from a larger sheet of a third material. Alternatively, the foam blocks may be molded in their desired shapes using any conventional foam forming process.

Optionally, the process 500 may further include Block 508 that represents finishing of the disposable oral care implement. In one embodiment, if the oral care tool of the disposable oral care implement includes a central body having a plurality of bristle projecting radially outward from the central body, the plurality of bristles are inserted into the central body. In another embodiment, if the oral care tool includes a brush, the bristles of the brush will be inserted.

Furthermore, the foam/polishing block may be configured with the body in various ways. For example, FIG. 1A and FIG. 1B show that the foam block 104 is connected to the first end of the body 102 at or through the center of a surface of the foam block 104. FIG. 2A and FIG. 2B show that the polishing block 204 is attached to the first end of the body 202 by attaching a surface of the polishing block 204 to a surface of the first end of the body 202. Although two different configurations are described in this disclosure, it should be appreciated that these are merely illustrative examples. There is no limitation on the configuration of the disposable oral care implement so long as the foam/polishing block is reasonably connected/attached to one end of the body.

Although the example process 500 is described in terms of separate blocks or steps, these blocks or steps can be processed in combination or in parallel. For example, one or more oral care tools usable with the oral care implement may be co-molded or over-molded with the body of the oral care implement. Alternatively, the one or more oral care tools may be formed integrally with the body.

CONCLUSION

Although the example disposable oral care implements have been described in language specific to structural features and/or methodological acts, it is understood that the implements are not necessarily limited to the specific features or acts described. Rather, the specific features and acts are disclosed as illustrative forms of the implements. For example, while embodiments are described having certain shapes, sizes and configurations, these shapes, sizes and configurations are merely illustrative. Also, while one example production process is described, implements accordingly to the present disclosure may be made using any suitable production process.

What is claimed is:

1. A disposable oral care implement comprising:
   a body;
   a rounded foam block connected to a first end of the body, the rounded foam block comprising a plurality of protrusions and a flat surface, the plurality of protrusions being made of a material different from a material of the flat surface to allow different levels of deformation when the rounded foam block is pressed against a surface to be polished; and
   an inter-dental pick coupled to a second end of the body, the inter-dental pick including a central body having a plurality of conically shaped spikes projected radially outward from the central body,
   wherein the rounded foam block comprises a spherical body having the flat surface, wherein a first type of surface is to be polished using the flat surface and a second type of surface is to be polished using a curved surface portion of the spherical body.

2. The disposable oral care implement as recited in claim 1, wherein the inter-dental pick is configured to clean a cavity between surfaces.

3. The disposable oral care implement as recited in claim 2, wherein the inter-dental pick further includes a first oral care material, the inter-dental pick being further configured to apply the first oral care material to the cavity and/or the surfaces when cleaning the cavity between the surfaces.

4. The disposable oral care implement as recited in claim 3, wherein the first oral care material comprises a gel material, a paste material, or a strip of solid or semi-solid material.

5. The disposable oral care implement as recited in claim 3, wherein the rounded foam block comprises a second oral care material.

6. The disposable oral care implement as recited in claim 5, wherein the second oral care material comprises an oral cleaning strip, the oral cleaning strip being disposed on and/or around the rounded foam block.

7. The disposable oral care implement as recited in claim 5, wherein the second oral care material comprises an abrasive powder.

8. The disposable oral care implement as recited in claim 5, wherein the first oral care material is of a different material than the second oral care material.

9. The disposable oral care implement as recited in claim 5, wherein the rounded foam block is impregnated with a liquid material, a gel material, or a paste material.

10. The disposable oral care implement as recited in claim 1, further comprising one or more coatings of nanostructures or microstructures applied to the rounded foam block, the body and/or the inter-dental pick.

11. A disposable oral care implement comprising:
a body;
a polishing block attached to a first end of the body, the polishing block comprising an oral cleaning strip disposed on and/or around the polishing block, the polishing block comprising a plurality of protrusions and a flat surface, a protrusion located in a surrounding of the flat surface having a different softness than a protrusion located at a center of the flat surface; and
an inter-dental pick coupled to a second end of the body comprising a floss holder to hold a dental floss.

12. The disposable oral care implement as recited in claim 11, wherein the polishing block comprises a plurality of protrusions and a flat surface, the plurality of protrusions being made of a material different from a material of the flat surface to allow different levels of deformation when the rounded foam block is pressed against a surface to be polished.

13. The disposable oral care implement as recited in claim 11, wherein the oral cleaning strip comprises a strip of solid or semi-solid cleaning material.

14. A disposable oral care implement comprising:
a body;
a foam block attached to a first end of the body; and
an oral care tool coupled to a second end of the body, the oral care tool comprising a tongue scrapper, an interdental pick, a brush, a floss holder, and/or a gum stimulator; and
wherein the foam block comprises a first oral care material, the foam block being configured to polish a surface, and wherein the oral care tool further includes a second oral care material, the oral care tool being further configured to clean a cavity between surfaces and to apply the second oral care material to the cavity and/or the surfaces when cleaning the cavity between the surfaces.

15. The disposable oral care implement as recited in claim 14, wherein the foam block and/or the oral care tool are selectively removable so as to be interchangeable with one or more other oral care tools.

16. The disposable oral care implement as recited in claim 14, wherein the foam block comprises a plurality of protrusions and a flat surface, a protrusion located in a surrounding of the flat surface having a different softness than a protrusion located at a center of the flat surface.

17. The disposable oral care implement as recited in claim 14, wherein the foam block comprises a plurality of protrusions and a flat surface, the plurality of protrusions being made of a material different from a material of the flat surface to allow different levels of deformation when the foam block is pressed against a surface to be polished.

18. The disposable oral care implement as recited in claim 14, further comprising one or more coatings of nanostructures or microstructures applied to the foam block, the body and/or the oral care tool.

19. The disposable oral care implement as recited in claim 14, wherein the first oral care material comprises a gel material, a paste material, or a strip of solid or semi-solid material.

20. The disposable oral care implement as recited in claim 14, wherein the first oral care material, the second oral care material or both comprises an abrasive powder.

21. The disposable oral care implement as recited in claim 14, wherein the first oral care material is of a different material than the second oral care material.

22. The disposable oral care implement as recited in claim 14, wherein the foam block is impregnated with a liquid material, a gel material, or a paste material.

* * * * *